United States Patent
Inan (10) Patent No.: US 11,737,796 B2
(45) Date of Patent: Aug. 29, 2023

(54) PROXIMAL FEMORAL DE-ROTATION NAIL

(71) Applicant: TST RAKOR VE TIBBI ALETLER SANAYI VE TICARET LIMITED ŞIRKETI, Istanbul (TR)

(72) Inventor: Muharrem Inan, Kartal Istanbul (TR)

(*) Notice: Subject to any disclaimer, the term of this patent is extended or adjusted under 35 U.S.C. 154(b) by 254 days.

(21) Appl. No.: 17/045,221

(22) PCT Filed: Mar. 26, 2019

(86) PCT No.: PCT/TR2019/050196
§ 371 (c)(1),
(2) Date: Oct. 5, 2020

(87) PCT Pub. No.: WO2020/117148
PCT Pub. Date: Jun. 11, 2020

(65) Prior Publication Data
US 2021/0068876 A1    Mar. 11, 2021

(30) Foreign Application Priority Data
Apr. 4, 2018   (TR) .................................. 2018/04792

(51) Int. Cl.
*A61B 17/72*     (2006.01)
*A61B 17/17*     (2006.01)
*A61B 17/88*     (2006.01)
*A61B 17/68*     (2006.01)

(52) U.S. Cl.
CPC ...... *A61B 17/7225* (2013.01); *A61B 17/1725* (2013.01); *A61B 17/725* (2013.01); *A61B 17/8872* (2013.01); *A61B 2017/681* (2013.01)

(58) Field of Classification Search
CPC ............ A61B 17/1725; A61B 17/7225; A61B 17/7241; A61B 17/7283
See application file for complete search history.

(56) References Cited

U.S. PATENT DOCUMENTS

| 4,858,602 A | * | 8/1989 | Seidel ............... A61B 17/7241 606/62 |
| 6,443,954 B1 | | 9/2002 | Bramlet et al. |
| 2002/0099379 A1 | | 7/2002 | Adam |

(Continued)

FOREIGN PATENT DOCUMENTS

CN    105615979 B    1/2018

*Primary Examiner* — Julianna N Harvey
(74) *Attorney, Agent, or Firm* — OPPENHUIZEN LAW PLC; David L. Oppenhuizen (57) ABSTRACT

The invention relates to the intramedullar nail fixation (13) of the femoral bone that is used in the field of orthopedics and traumatology, in particular, in the pediatric orthopedics field; Its features include the follows; Removal of many negativities in the treatments of femoral proximal area fractures seen in the child age group, young and old bone rotation surgeries, malunion, nonunion and deformities, and in order to make positive contribution to the healing processes of patients, the proximal femoral de-rotation nail (13), by which location can be fixed by turning in an angular way, and by which the operator can perform rotation as much as necessary by fixing rotation angle, and which is formed with the proximal component (1) and the distal component (2), which can perform rotational movement on each other and can fix its location, was developed.

3 Claims, 7 Drawing Sheets

(56) References Cited

U.S. PATENT DOCUMENTS

| | | | |
|---|---|---|---|
| 2005/0055024 A1* | 3/2005 | James | A61B 17/1668 606/64 |
| 2009/0318926 A1* | 12/2009 | Christie | A61B 17/1725 606/96 |
| 2012/0165880 A1* | 6/2012 | Levy | A61B 17/7233 606/300 |
| 2012/0226278 A1* | 9/2012 | Nardini | A61B 17/7241 606/64 |
| 2013/0046311 A1* | 2/2013 | Blake | A61B 17/1725 606/86 R |
| 2016/0199108 A1* | 7/2016 | Matsuda | A61B 17/72 606/62 |
| 2017/0007303 A1* | 1/2017 | Hansson | A61B 17/725 |
| 2019/0038326 A1* | 2/2019 | Hedgeland | A61B 17/1721 |
| 2020/0323568 A1* | 10/2020 | Daly | A61B 17/7241 |

* cited by examiner

PROXIMAL FEMORAL DE-ROTATION NAIL

CROSS REFERENCE TO RELATED APPLICATIONS

This is a National Stage of International Application No. PCT/TR2019/050196, filed Mar. 26, 2019, which claims priority to Turkish Patent Application No. 2018/04792, filed Apr. 4, 2018, the entire disclosures of which are hereby incorporated by reference in their entirety.

BACKGROUND OF THE INVENTION

Technical Area

The present invention; It is related to femoral bone intramedullary fixation nail used in the field of orthopedics and traumatology, especially in the field of pediatric orthopedics.

The invention, especially, relates to a new proximal femoral de-rotation nail which provides new advantages by surpassing a lot of technical problems.

Description of Known Status of the Technique

In the field of orthopedics and traumatology, in the present case, plate-screw fixation, elastic pins, external fixators and locking nails are used for the applications such as the femoral bone fractures and osteotomy etc.

Since the remodulation capacity of the ages of 4-5 is extremely high in children, the conservative treatment method, with plaster, is applied. For ages of 5-12, whereas the use of elastic nail implant method is recommended, for patients over the age of 12, the use of rigid locking nails, plates or fixators are preferred.

Plate indication: They are multi-part unstable fractures, very distal, very proximal region fractures. Because the application of plate-screws currently used requires a large incision, there is a high risk of infection and there also are risks of further damaging the soft tissue.

Moreover, there are risks such as late mobility after plate application, delayed union of the fracture or osteotomy area, or even that of nonunion.

Fixator indications are recommended in patients suffering from soft tissue problems, in the presence of open wounds, in overweight patients, in segmental fractures, and in intensive care patients. Apart from these, external fixators, which are applied in the present situation, have negative aspects such as being out of the skin, preventing patient movements and hindering patient comfort.

Elastic nails can provide insufficient stability intramedullary placement due to their structure; and may cause adverse conditions such as migration (spread) to soft tissue or adjacent joints.

Rigid intramedullary nailing can vary depending on the manufacturer company, the diameter of the rigid nails varies from 8 mm to 16 mm and their lengths are between 24 cm and 50 cm in general. The nail diameters increase by 1 mm of difference and the nail length increases by 2 cm of difference. locking rigid nails made of titanium are designed to be straight or curved. Each nail produced by various companies has its own unique design.

The entry point of the nail varies according to the design of the selected nail. The entry point of the existing nails is generally, according to their proximal distal anterior posterior and lateral profile appearance, the piriformis fossa located between the trochanter major or major and the femoral neck. However, the vascular structure, which is near this entrance, leads to undesirable problems such as the risk of damaging the vascular network maintaining the femoral head and the soft tissues, which need to be protected. Especially in overweight patients, this nail entrance point is a major cause of difficulty.

Existing locking nails are in the form of one piece and they do not, during nail fixation or after locking, allow rotational (rotation) correction between the distal and proximal fragments which may be required between the bone fragments.

Pathology the varus at the upper end of the femoral may require de-rotation osteotomy. In other words, to correct the femoral anteversion at the upper end of the thigh, the femur is cut and rotated around its vertical axis (de-rotation) and the increased angle between the femoral neck and the body is reduced by removing a bone wedge in a way that its bottom end remains inside (the varus).

There has been a need to develop a femoral bone intramedullary fixation femoral de-rotation nail that eliminates the deficiencies and disadvantages of the products mentioned above and used in the field of pediatric orthopedics, and that meets the needs of the operator and the patient in a superior way.

In the patent application, with the number of TR 2015/14428, and with the name of "long bone de-rotation device"; This invention relates to a long bone de-rotation device which is developed with the aim of removal of orthopedic deformities, and which provides fixation of the bone rotation angle during surgery in bone turn operations. However, a de-rotation device is mentioned here. It is not a solution for developing a nail.

DESCRIPTION OF THE OBJECTIVES OF THIS INVENTION

The objective of this invention is, by looking at the known situation of the technique, to develop a proximal femoral de-rotation nail which has many advantages, by which the disadvantages of existing structures are eliminated.

Another object of the invention is to eliminate the risk of damaging the blood vessels and the soft tissues, needing to be protected, near the piriformis fossa seen in the existing nail applications that are performed by using the lateral trochanteric entrance point in the bone.

Another object of the invention is to facilitate the application of the nail, especially in overweight patients, and to contribute positively to the healing process of the patient.

A further object of the invention is to enable a rotational (rotation) correction between the distal and proximal fragments that may be needed among bone fragments during proximal femoral de-rotation nail fixation or after locking process.

A further object of the invention is to design a developed proximal femoral de-rotation nail in a way that is holistic, and having constricting distal end and proximal slope, and that is in a suitable structure in sagittal and coronal plan for child proximal femoral bone anatomy, and that can provide an easy access.

A further object of the invention is, compared to existing nails, to provide additional bone stability, against the rotational, compression, tensile and shear forces of the fractured bone fragment, by providing adequate fixation and high-quality stability and firm retention, and provides additional bone stability.

In order to achieve the abovementioned objectives, a pediatric proximal femoral de-rotation nail, which has significant advantages that eliminate a lot of disadvantages in the treatment of femoral proximal area fractures, malunion, nonunion and deformities seen in the pediatric age group, a lot of disadvantages in the treatment deformities, and which contributes positively to the healing process of patients, has been developed.

| Reference Numbers | |
|---|---|
| 1 | Proximal component |
| 1/1 | Proximal threaded end |
| 1/2 | Groove structure |
| 1/3 | Locking screw hole |
| 1/4 | Guide connection line |
| 1/5 | Linear line sign in the proximal |
| 1/6 | Inner grooved slot |
| 2 | Distal component |
| 2/1 | Distal threaded end |
| 2/2 | Linear line sing on distal |
| 2/3 | Static locking holes |
| 2/4 | Inner threaded slot found in distal |
| 3 | Connection bolt |
| 3/1 | Head part |
| 4 | Nail end cap |
| 5 | Exterior targeting guide arm |
| 6 | De-rotation measurement guide |
| 7 | De-rotation gauge |
| 8 | Screwdriver |
| 9 | Numbers on screwdriver |
| 10 | K-wire |
| 11 | Bone locking screws |
| 12 | Alignment bars |
| 13 | Nail |

DETAILED DESCRIPTION OF THE INVENTION

The developed nail (13) has a design consisting of two components, the proximal component (1) and the distal component (2), so as to easily provide the proximal femoral anti-version angling during application.

Figure 7:
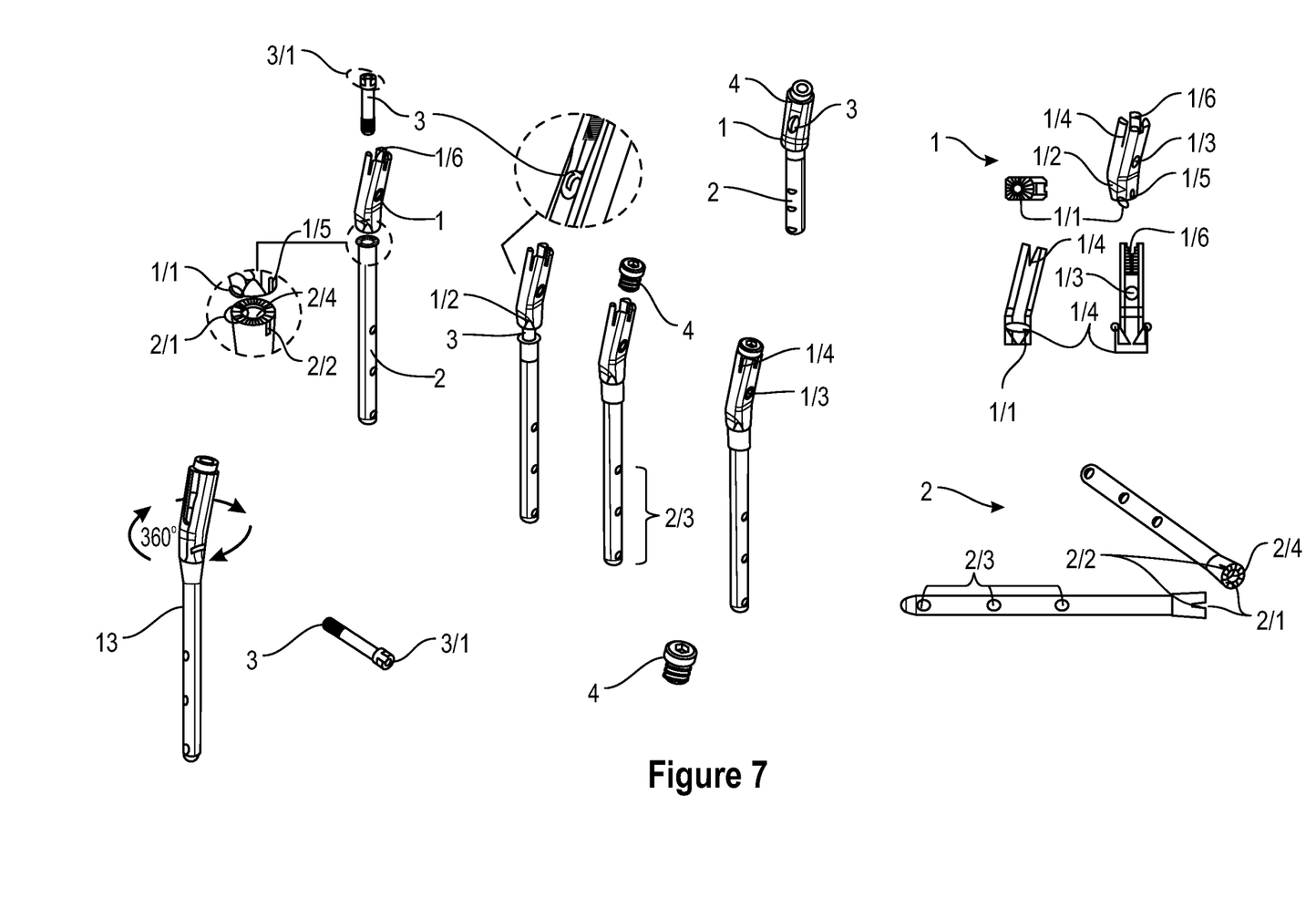
FIG. 7 is a series of exploded views of the distal component and the proximal component of the derotation nail.

As shown in FIG. 7, the distal component (2) and the proximal component (1) are formed as a special threaded joint as the proximal threaded end (1/1) and the distal threaded end (2/1).

This structure controls rotation through the connecting bolt (3) between the two distal components (2) and the proximal component (1) and provides certain and desired dimensions of adjustments and rotation movement. In this way, the necessary rotational correction between bone fragments can be carried out.

Figure 2:
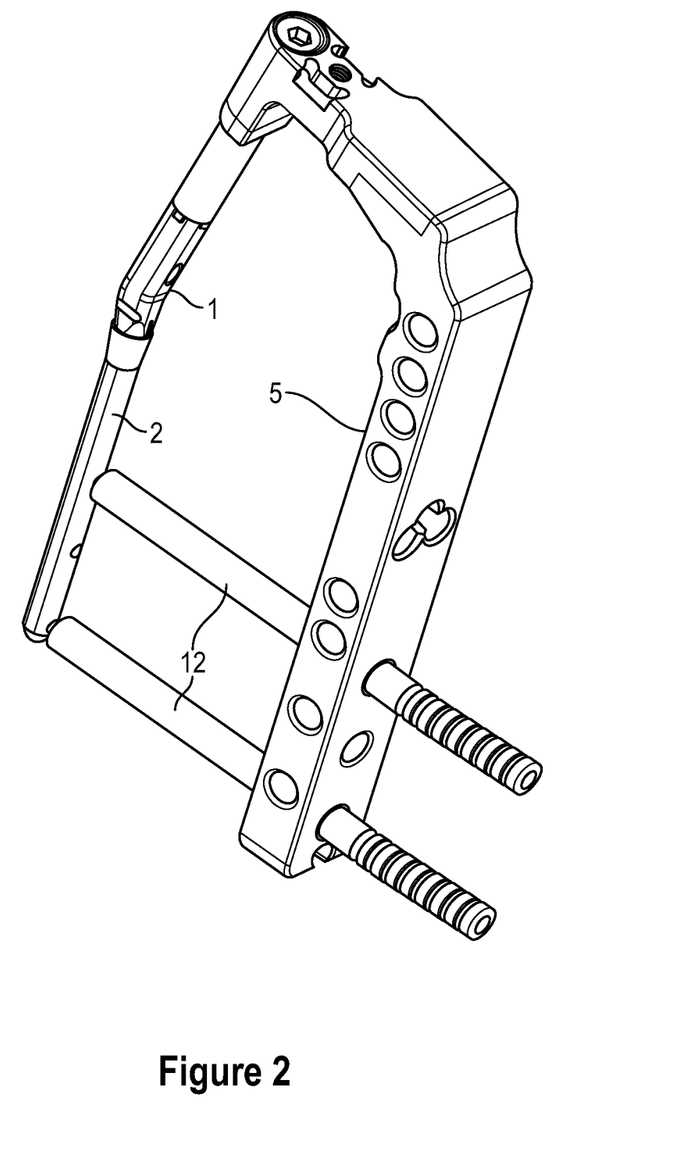
FIG. 2 is a perspective view showing the derotation nail and external targeting guide as in FIG. 1, and further including special tip alignment bars to assist in aligning the distal component of the derotation nail according to a representative application of the invention.

The degree of the rotational correction can be monitored, from outside of the skin, with a de-rotation gauge (7) by the help of K-wire (10) that is sent to the bone through the de-rotation measurement guide (6) which is mounted to the distal of the exterior targeting guide arm in FIG. 2.

Through the exact tightening of the connection bolt (3) after the desired correction, the movement between the proximal component (1) and the distal component (2) can be completely prevented by creating a stable structure.

Figure 5:
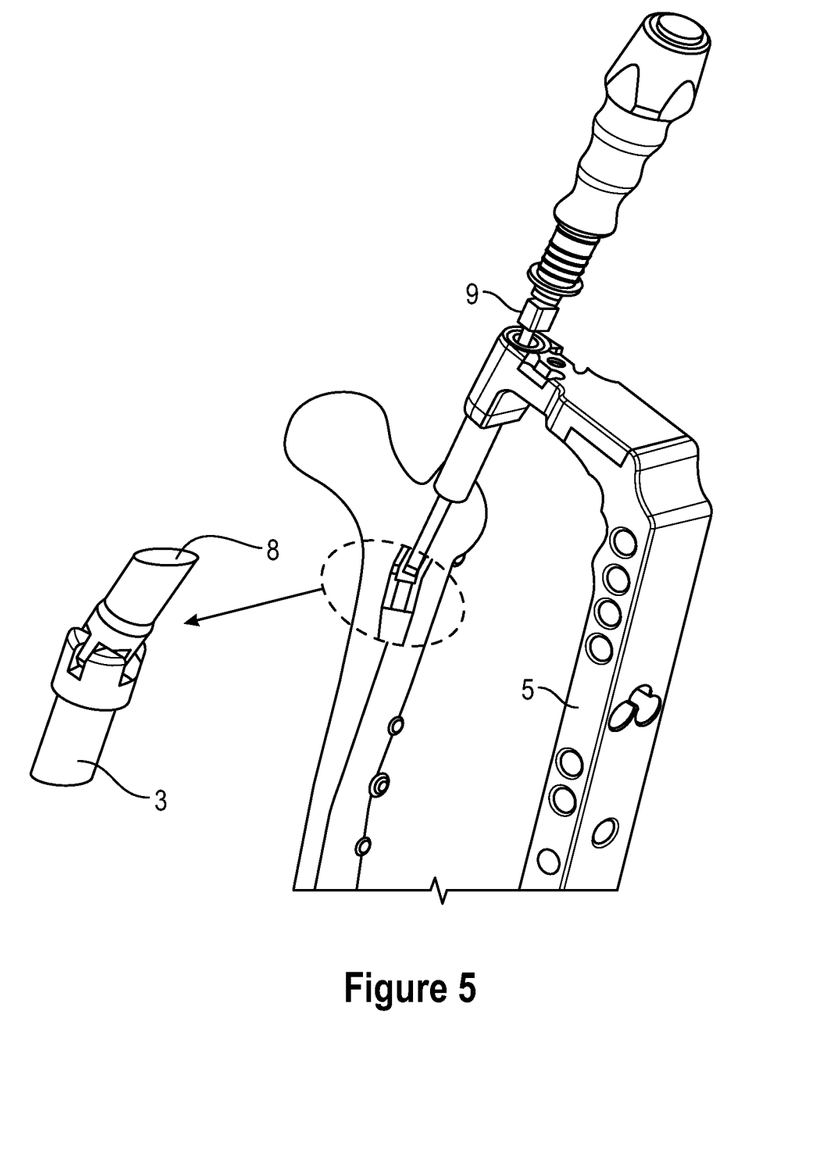
FIG. 5 is a schematic view showing the screwdriver inserted through a portion of the external targeting guide and coupled with a connection bolt of the derotation nail to selectively tighten or loosen the distal component and the proximal component of the derotation nail to one another.

The head part (3/1) of the connection bolt (3) has been processed as a special + sign by emptying, and again with a special + protrusion processed sender screwdriver (8) tip, a feature of operating even in angled planes is enabled.

By means of this feature, while the nail (13) is inside the bone, it is possible to enter through the incision at the entrance of the nail (13) and to forward along the channel of the nail (13) proximal component (1) and to reach the connecting bolt (3), and thus enables the connection bolt (3) to be loosened and tightened. The numbers on the screwdriver (9) ensure that the loosening and tightening ratings can be monitored. In this way, the structure of the total nail (13) can be provided in a way that at least 12 degrees of angling occur between the proximal component (1) and the distal component (2) in terms of anteroposterior.

This angular feature allows, in the normal femoral neck anatomy, during the nail (13) application, the bone entrance place to be in lateral of sharp point of the major trochanter in the anteroposterior view, and it to be in the alignment of medullary channel in the lateral view.

Since the pediatric proximal femoral de-rotation nail (13), in this feature, is applied using the lateral trochanteric entrance point, the risk of injury to the blood vessels near the piriformis fossa seen in the existing nail (13) applications, is prevented. It also offers the possibility to be used in the proximal femoral varus and valgus deformity corrections. The difficulty of application in overweight patients is thus eliminated.

Figure 1:
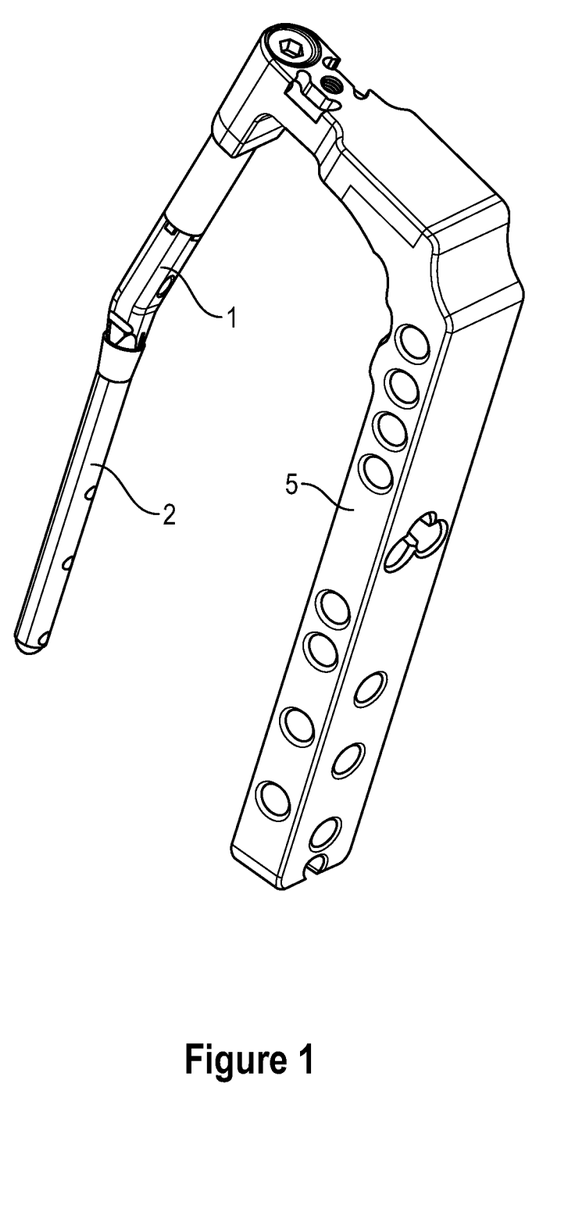
FIG. 1 is a perspective view of an exemplary derotation nail mounted onto an exemplary external targeting guide according to a representative application of the invention.

The nail (13) is mounted on the exterior targeting guide arm (5). Then, the lateral trochanteric entrance place is opened with the carving devices and the nail (13) is inserted into the bone.

The holistic shape of the joint and the nail (13), the constricting tip shape and the proximal slope are designed to make the most suitable and easy entry in the sagittal and coronal plane to the pediatric proximal femoral bone anatomy.

Figure 6:
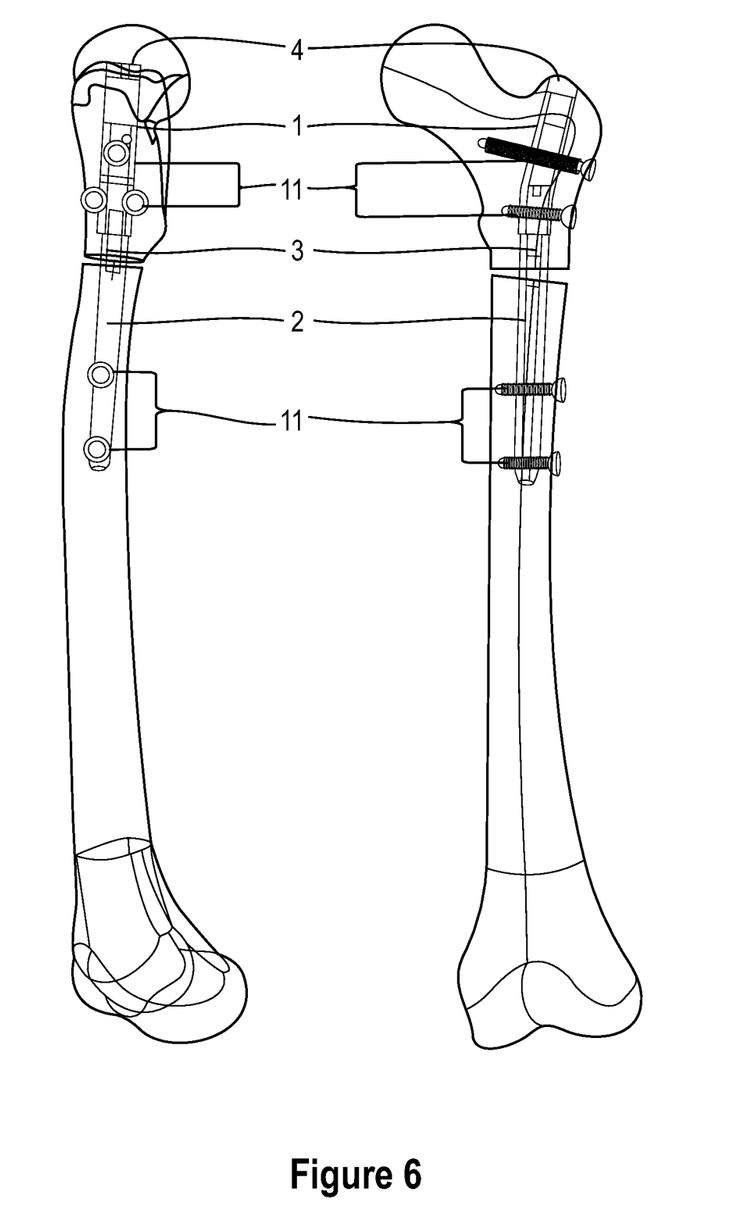
FIG. 6 is a schematic view drawing of the derotation nail and locking screws located inside the femoral bone in the sagittal and coronal plan.

The geometric design of the nail (13) and the position of the bone locking screws (11) inside the bone were created to maximize fixation of the bone fragments.

To increase the rotational stability in the proximal fragment, the proximal component (1) of the nail (13) is designed as being square cross-section. In accordance with the variable bone structure of the patient, at least three different thicknesses of proximal component (1) measurements can be created, which offers the operator an option. Otherwise, while insufficient stability situations of the nails (13) can be seen in the large bones, the use of the same sized nail (13) in the small structured bone may result in excessive bone defect.

For rotational, compression, tensile and shear forces of the proximal bone fragment, a special nail (13) on the proximal component (1) is provided for fixation and stability and a locking screw hole (1/3) that is directed to a femoral neck is provided for bone locking screws (11) and two groove structures (1/2) are, parallel to one another, formed.

Through applying bone locking screws (polar-support screwing) (11) from the groove structure (1/2) located at the anterior and posterior of the proximal component (1) and through providing a more rigid retention to the strong bone structure in the medial of the neck, additional bone stability is, with this nail (13), provided, compared to the existing nails (13).

Rigid fixation allows the patient to give early load on the leg. In the event of a delayed bone union, it will be possible to make a dynamization by removing one of the screws on the side which is closer to the fracture/osteotomy line. Since the nail (13) fills the bone marrow, there will be no angular deformity.

The nail (13) is designed as being grooved and in different sizes in order to provide the bone locking screws (11) fixation.

The distal component (2) of the nail (2) offers at least three different lengths (100-125-150 mm) and at least three different diameters (Ø 8-9-10 mm) in order to provide options for the patient needs and operator in terms of the variable patient bone channel structure.

There are at least three static locking holes (2/3) on the distal component (2). By means of these static locking holes (2/3) on this multiple distal, a higher rate of fixation is provided against the rotatable, compression, tensile and shearing forces, compared to distal fragment other existing nails (13).

There are some risks such as increased infection risk and greater damage to the soft tissue due to delayed mobility, delayed union of the fracture or osteotomy area, nonunion, and large incision that can be seen in applications of existing plates that are used in nail (13) indications.

The nail (13), subject of the invention, is applied with a more minimally invasive technique when compared to the above-mentioned risky systems. Therefore, it minimizes undesired risks and provides early mobility in normal or disabled children because of obtained stability.

At the end of the application of the nail (13), there are nail end cap (4), designed at least in three different dimensions, and that are placed at the top of the nails (13). They prevent the filling of the inner grooved housing (1/6) with bone tissue at the nail (13) peak point, which causes significant difficulty during removal of the nails (13) after the healing and thus provide facility for the operator and saves time during the operation.

An external targeting guide arm (5) instrument is designed for the application of the nail (13) and bone locking screws (11) with minimal incision technique. This instrument has a laser line that matches the connection end of the nail (13).

A correct nail (13) installation is provided for anatomic application by matching this line and the guide connection line (1/4) on one side of the top of the nail (13). The nail (13) is designed in a way that its head has four protrusion and its internal is in the form of grooved slots (1/6). In this way, the exterior targeting guide arm (5) provides complete placement by matching the end of the instrument to this place (providing complete matching with the grooves of the upper screw).

In this installation, in order to adjust to the lateral appearance of the nail (13) and to confirm that the proximal component (1) and the distal component (2), the two components are in the correct plane, it is mounted in a way that the rectilinear linear signs (1/5) at the proximal that can outwardly be seen in the lateral of joint places of components, and that can form signs in the form of linear line when matched one another, can be seen. For this purpose, the special end alignment bars (12), which are sent to the distal component (2) by means of the external targeting guide arm (5) and provide alignment, have been formed.

The surgical application technique of the nail (13) is as follows:

The negative impact of femoral anteversion on hip instability and walking is removed by cutting femur from the trochanter minor level and by turning it around its long axis (femoral de-rotation osteotomy). In the event that a bone wedge is removed from the upper end of the femoral in a way that its base remains inside, the coxa valga, seen in cerebral palsy patients, is corrected and covering femoral head is increased.

The proximal component (1) of the nail (13) has a 12° lateral opening in comparison to the distal component (2) of the nail (13). Because of its this feature, the nail (13) entrance place is of importance in terms of surgery planning. According to this; nail (13) entrance place, for de-rotation application, should be 2 mm lateral of the large trochanter type.

Figure 3:
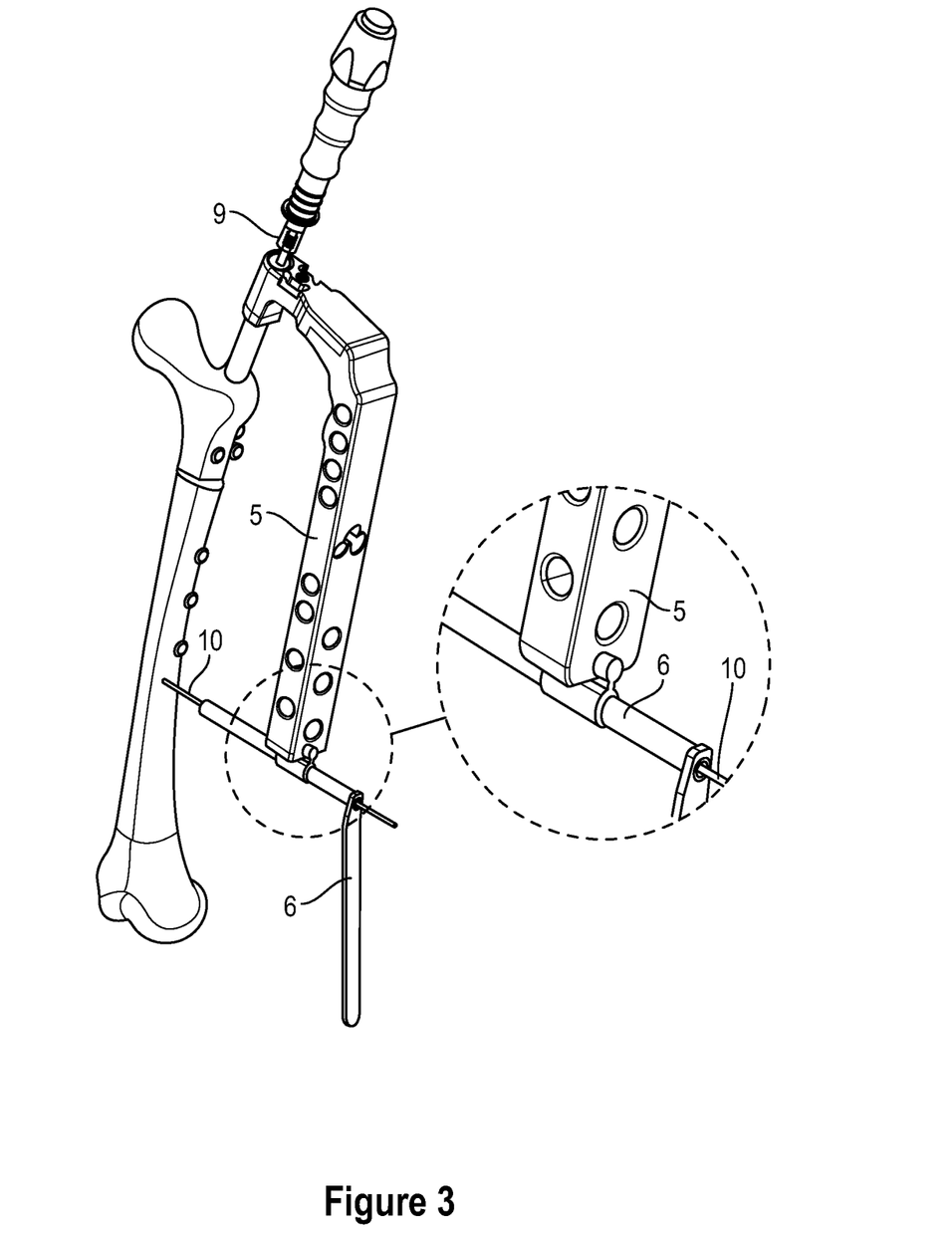
FIG. 3 is a schematic view of a k-wire attached to the derotation nail and the external targeting guide.

Nail (13) entrance place for the application of the varus should be 6-7 mm from the lateral of the large trochanter type. At the AP view, the end of the k-wire (10) (guide wire) should be in the position to center the medullary channel at the trochanter minor level.

The nail (13) entrance place is opened using the reamer devices. In the event that de-rotation correction is to be made, anteversion angles are determined by sending the K-wire (10) at neutral angles to the neck in parallel and proximal in the femoral condyle before osteotomy.

After osteotomy, during correction, these K-wires (10) are used as a guide by being monitored from outside the skin. At the level of trochanter minor, osteotomy is performed in such a way that it is below the minor.

In the set, the flexible long cannulated reamer devices and the distal fragment are prepared as being suitable for the nail (13). The nail (13) is mounted to the outer targeting guide arm (5).

The nail (13) installation must be performed so that the laser line on the junction place between the proximal component (1) and the distal component (2) is identical to one another. The alignment bars (12), which are to be used in this installation, are placed to the distal static locking holes (2/3) located on the exterior targeting guide arm (5), and the installation of the nail (13) is completed with the intermediate bolt (3).

The nail (13) is inserted into the intramedullary canal by the help of external targeting guide arm (5). In the final position, the nail (13) is advanced so that the top of the nail is placed at the bone level. It is necessary that the osteotomy line be 1 cm distal of the nail (13) joint juncture. Distal locking screws are inserted using appropriate procedures for its technique. Distal locking is done at three different levels and statically.

After applying the distal locking screws of the nail (13), the intermediate connection bolt (3) merging the proximal to the distal component (1,2) of the nail (13), is loosened by using the special numbered screwdriver (8) (numbers 1-2-3-4 on it and its marked tip in the form of +)

The number on the screwdriver (9) on it must be observed during this loosening process. According to the direction of view on the number section of the screwdriver (9); if the visible number is on 1, it is loosened by turning on the opening way until 3. In the meantime, the range of loosening between the proximal and distal component (1,2) should be seen in the scopy control.

Figure 4:
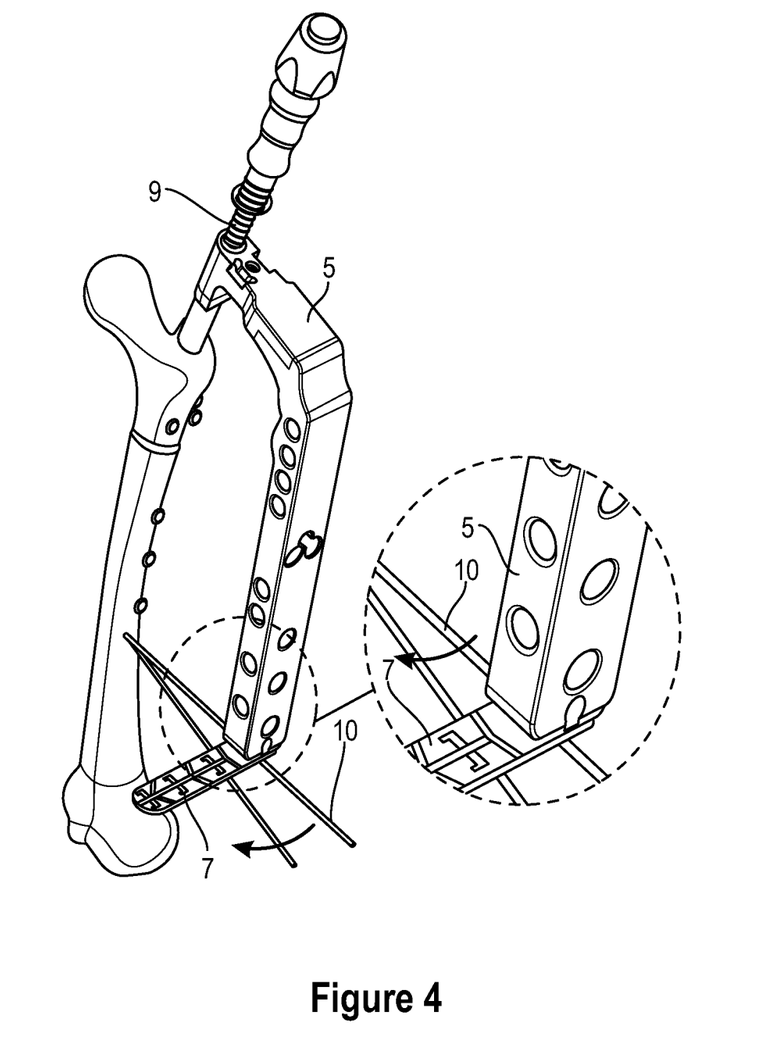
FIG. 4 is a schematic view of a de-rotation gauge apparatus.

The knee patella should be in the forward position while the leg foot fingers looks upwards. The femoral de-rotation correction is performed until the appropriate degree. This correction can be monitored by means of the de-rotation gauge (7) located onto distal of the exterior targeting guide arm (5) of the nail (13).

The junction place between the proximal and distal components (1,2) is in the threaded notch design which prevents rotation when a full connection is provided. When the intermediate bolt (3) is loosened, each notch provides an angular rotation of 12° in the rotation between the proximal-distal components (1,2).

After de-rotation correction, the intermediate connection bolt (3) is tightened by using its special screwdriver (8). The numbers on the screwdriver (9) must be restored in this process. The connection between the proximal and distal components (1,2) should be clearly seen in the scopy.

Proximal component (1) fixation is carried out through the locking screws in the specified lengths. The external targeting guide arms (5) and the entire instrumentation are removed by being taken out of the nail (13). The end cap (13) is fitted with the top screw at the end.

The screw placements are carefully confirmed through the scopy control at the front and rear views. Some important points such as extremity length, alignment, de-rotation, foot toe and knee patella status are controlled and incision area closed according to the layer anatomy. In this way, thanks to the developed nail (13) and the application apparatus that is suitable for the nail (13), the operator can facilitate the operation, and the patient can undergo surgery with fewer risks.

The invention relates to the intraluminal fixation nail (13) of the femoral bone that is used in the field of orthopedics and traumatology, in particular, in the pediatric orthopedics field; Its features include the follows; Removal of many negativities in the treatments of femoral proximal area fractures seen in the child age group, young and old bone rotation surgeries, malunion, nonunion and deformities, and in order to make positive contribution to the healing processes of patients, the proximal femoral de-rotation nail (13) was formed by which location can be fixed by turning in an angular way, and by which the operator can perform rotation as much as necessary by fixing rotation angle, and which is formed with the proximal component (1) and the distal component (2), which can perform rotational movement on each other and can fix its location.

In order to enable it to perform the necessary rotational correction among bone fragments through its being adjusted in certain and desired dimensions and performing rotation movement a threaded structure was formed in a way of at least one connecting bolt (3) between the distal component (2) and the proximal component (1), which controls the rotation, and inner threaded slot (2/4) placed on distal by which the connection bolt (3) enables the connection by advancing through the distal component (2), the proximal threaded end (1/1) and the distal threaded end (2/1) at the connection ends of the distal component (2) and the proximal component (1).

The head portion (3/1) of the processed connection bolt (3), which was formed in the form of a + sign, and which can operate even in angular places through the head of + protrusion sender screwdriver (8), was formed.

A holistic nail (13) structure was formed in a way that, when the nail (13) is in the bone, entering process is made through the incision area at the entrance of the nail (13) and moves along the channel of the nail (13) proximal component (1) and reaches to the connecting bolt (3) and enables the connection bolt to be loosened and tightened and enables loosening and tightening degrees to be monitored by the help of numbers on the screwdriver (9), and that at least 12 degrees of angulation can be present between the proximal component (1) and the distal component (2) in anteroposterior view.

In order to prevent the risk of injury to the blood vessels near the piriformis fossa, and also to remove the difficulty of application in overweight patients by offering the possibility of use in the proximal femoral varus and valgus deformity corrections; the distal component (2) and the proximal component (1), which are applied by using lateral trochanteric entry point, were formed in a way that, during the application of the nail (13), the entry place to the bone is in the lateral of sharp point of the major trochanter in anteroposterior view and in the medullary canal level in lateral view.

The distal component (2) and the proximal component (1), which enables the most appropriate and easy access to the pediatric proximal femoral bone anatomy in in the sagittal and coronal plane through the narrowed tip shape and proximal slope, have been formed.

Bone locking screws (polar-support screwing) (11) are formed from the groove structure (1/2) located at the anterior and posterior of the proximal component (1), providing a more rigid retention to the strong bone in the medial of the bone and additional bone stability.

At least one static locking hole (2/3) is formed on the distal component (2), which provides higher rate of fixation of the distal bone fragment against rotational, compression, tensile and shear forces.

The locking screw hole (1/3) directed towards the femoral neck for the bone locking screws (11) on the proximal component (1) and two groove structures parallel to one another was created for the fixation and stability of the proximal bone fragment against the rotational, compression, tensile and shear forces of the proximal bone fragment (1).

The guide connection line (1/4) on one side of the nail (13) top, and nail (13) head with protrusion, enabling a correct nail installation for anatomic application by matching, and an internal threaded groove (1/6) were created.

In order to adjust to the lateral appearance of the nail (13) and to confirm that the proximal component (1) and the distal component (2) are in the correct plane, and it is mounted in a way that the rectilinear linear signs (1/5) at the proximal that can outwardly be seen in the lateral of joint places of components, and that can form signs in the form of linear line when matched one another, can be seen, were formed and linear line sign (2/2) was formed on distal in order to make the nail installation (13) in a way that the laser line on the junction place between the proximal component (1) and the distal component (2) is identical to one another.

In order to make the nail installation (13) in a way that the laser line on the junction place between the proximal component (1) and the distal component (2) is identical to one another, the alignment bars (12) used in the mounting process, and intermediate connection bolt that is fitted to the distal static locking holes (2/3) on exterior targeting guide arm (5) was created.

The external targeting guide arm (5), which enables the adjustment of the nail (13) in the bone and the de-rotation angle, in which the screwdriver (8), having a numbers (9) part on it, which allows the connection bolt (3) to be loosened and secured by the position adjustment, and the alignment bars (12), by which the position is adjusted and aligned according to the bone, and the de-rotation measurement guide (6), which enables the angle of rotation to be adjusted and the de-rotation meter (7) were formed.

At the top point of the nail (13), which causes a significant difficulty during removal of the nails (13) after healing, by preventing the inner grooved slot (1/6) from being filled with the bone tissue, and at the end of the nail application, which enables the time-saving while providing the operator with ease during the removal of the nail (13), the nail top screws (4) that are fitted to the top of the nails (13) were formed.

I claim:

1. In combination, an intramedullary de-rotation fixation nail for insertion in the femoral bone, and an external targeting guide arm for inserting the intramedullary de-rotation fixation nail into the femoral bone and adjusting the rotational position of the intramedullary de-rotation fixation nail to rotatably correct a deformity in the femoral bone, the combination including;

the intramedullary de-rotation fixation nail having a distal component, a proximal component, and a connection bolt for securing the proximal component to the distal component, the distal component and the proximal component being rotatably adjustable to one another, the distal component having a plurality of holes for receiving screws to lock the distal component to a distal portion of the femoral bone distal of an osteotomy line, and the proximal component defining an inner channel extending therethrough, the proximal component having an inner grooved slot at a proximal end, and the connection bolt being inserted into and partially through the inner channel in the proximal component, the connection bolt further being in threaded connection with the distal component to threadingly secure the distal component and the proximal component to one another; and the external targeting guide arm being mounted to the proximal component at the inner grooved slot, the external targeting guide arm further having a distal end including a de-rotation measurement guide, a de-rotation gauge, and a k-wire to measure the degree of rotation applied between a proximal portion of the femoral bone proximal of the osteotomy line and the distal portion of the femoral bone distal of the osteotomy line, the de-rotation measurement guide being mounted at the distal end of the external targeting guide arm, the k-wire extending through the de-rotation measurement guide and having an end that is configured to be secured into the distal portion of the femoral bone to accurately determine the rotational position thereof, the de-rotation gauge is also secured to the distal end of the external targeting guide arm and is oriented substantially perpendicular to the k-wire such that the position of the k-wire along the de-rotation gauge accurately displays the degree of rotation between the distal component and the proximal component in order to surgically correct a deformity in the femoral bone.

2. The combination of claim 1 wherein the proximal component has a square-shaped cross-section to increase the rotational stability of the proximal component that is configured to be secured within an upper fragment of the femoral bone.

3. The combination of claim 1 including a nail end cap secured onto the proximal component to close off the inner channel to prevent bone tissue from filling the inner channel.

* * * * *